United States Patent [19]

Dorr et al.

[11] Patent Number: 5,062,852
[45] Date of Patent: Nov. 5, 1991

[54] TIBIAL PROSTHESIS WITH INDEPENDENT MEDIAL AND LATERAL BASEPLATES

[75] Inventors: Lawrence D. Dorr, La Canada, Calif.; Brian D. Burkinshaw, Pflugerville; Joseph S. Skraba, Austin, both of Tex.

[73] Assignee: Intermedics Orthopedics, Inc., Austin, Tex.

[21] Appl. No.: 477,745

[22] Filed: Feb. 9, 1990

[51] Int. Cl.$^5$ ............................................. A61F 2/38
[52] U.S. Cl. ..................................................... 623/20
[58] Field of Search ...................... 623/16, 17, 18, 20

[56] References Cited

U.S. PATENT DOCUMENTS 4,944,757  7/1990  Martinez et al. ...................... 423/20

FOREIGN PATENT DOCUMENTS 3730175  9/1988  Fed. Rep. of Germany ........ 623/20
2632516 12/1989  France ................................... 623/20
2219942 12/1989  United Kingdom .................. 623/20

Primary Examiner—David J. Isabella
Attorney, Agent, or Firm—John R. Merkling

[57] ABSTRACT

A tibial prosthesis with independent medial and lateral baseplates. The baseplates can be coupled together for simultaneous implantation using an implantation apparatus. A high-molecular weight polyethylene upper part with articulating surface can then be attached both to the baseplates and to the tibia. The resulting prosthesis can conform to the stabile condition of the tibia without rocking in the baseplates. Bony ingrowth from the tibial head into special surfaces of the baseplates securely attaches the baseplates to the tibial head and the possibility of diminished fixation is reduced.

49 Claims, 3 Drawing Sheets

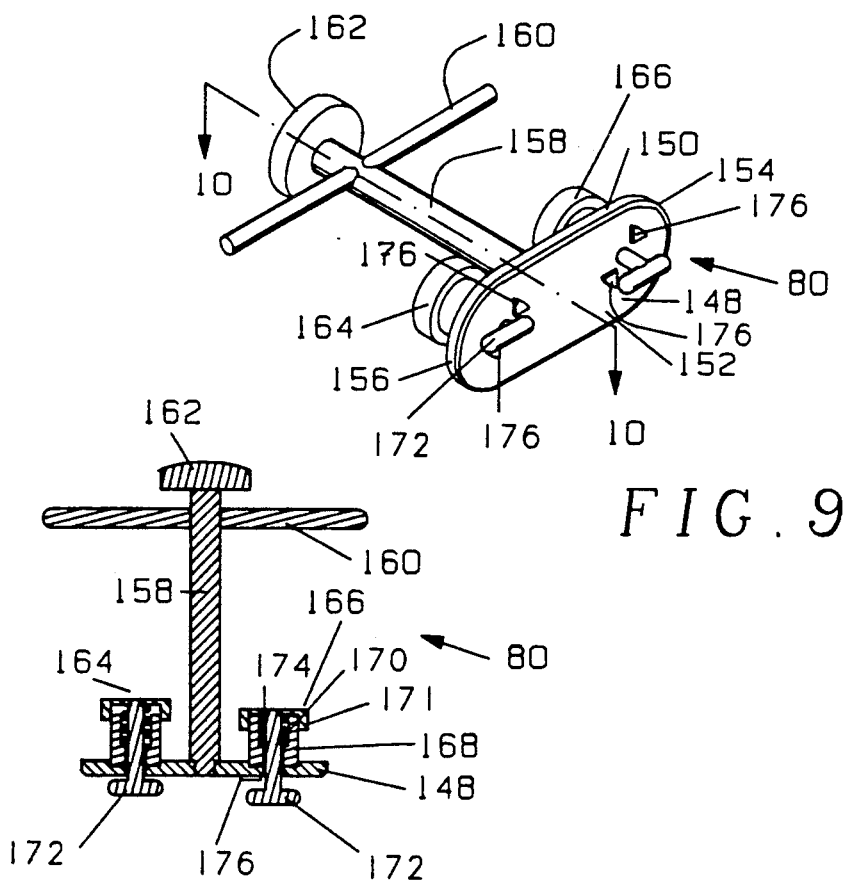
FIG. 9
FIG. 10
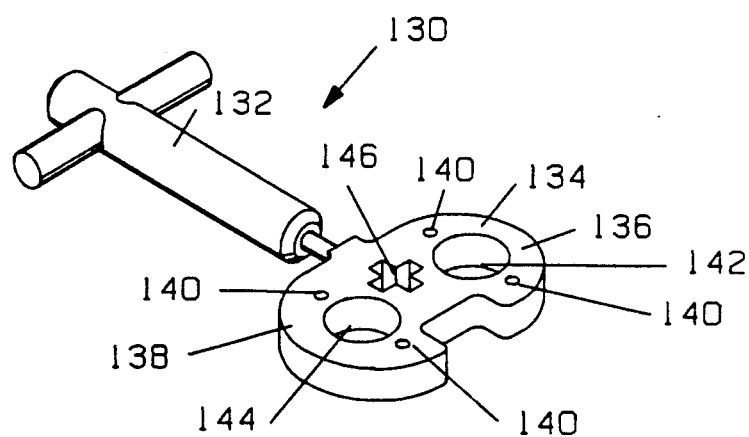
FIG. 8

TIBIAL PROSTHESIS WITH INDEPENDENT MEDICAL AND LATERAL BASEPLATES

BACKGROUND OF THE INVENTION

Our invention is in the general area of orthopedic prostheses, and in particular tibial prostheses.

The tibia is situated at the front and inner side of the leg and, except for the femur, is the longest and largest bone in the skeleton. It is prismoid in form, expanded above, where it enters into the knee joint. The head of the tibia is large and is expanded on each side into two eminences, the tuberosities. These present two smooth concave surfaces which articulate with the condyles of the femur. The medial condyle is more prominent anteriorly and broader both in the anterior-posterior and transverse diameters than the lateral condyle. Accordingly, the lateral articular surface of the tibia is longer, deeper and narrower than the medial surface of the tibia, so as to articulate with the lateral condyle. The medial surface is broader and more circular, concave from side to side, to articulate with the medial condyle. The anterior surfaces of the tuberosities are continuous with one another, forming a single large surface which is somewhat flattened. Posteriorly the tuberosities are separated from each other by a shallow depression for attachment of ligaments. The inner tuberosity presents posteriorly a deep transverse groove for the insertion of a tendon.

Through aging or disease, the articulating surfaces of the femur and the tibia may degrade, and replacement with the prostheses may be necessary. Numerous designs for prostheses have been proposed, but none has gained universal acceptance. There remains room for improvement, particularly because of the interaction between biological structures and a prosthesis.

For example, when a tibial prosthesis is implanted, it is a common practice to resect the head of the tibia. The surgeon usually removes the tuberosities by sawing across the head of the tibia with a sagittal saw. This produces a relatively flat surface, preferably perpendicular to a mechanical axis of the tibia so that the forces produced in the knee joint will be generally uniformly distributed. The bone of the tibia, however, is not uniform in character. The outer surface is less porous than the inner and is called cortical bone. The more porous inner portion is called cancellous bone. The cancellous bone is somewhat spongy and forms a lattice work within the cortical bone. At the head of the tibia, the cortical bone has both an irregular upper surface and a varying thickness. When the tibial head is resected, the structural characteristics of the upper surface of the tibia are altered. In some places, the cortical bone may be completely removed, and the inner cancellous bone exposed. The thickness and strength of the cortical bone will be altered. Because of the variation between individuals, as well as the effects disease and aging, the strength of a particular resected surface is unpredictable. The structural characteristics of the tibia supporting the prosthesis affect the long-term viability of the prosthesis.

Traditionally, tibial prostheses have comprised a rigid metal baseplate to be affixed to the resected upper surface of the tibia and an ultra-high molecular weight polyethylene upper part with articulating surface which attaches to the baseplate. We have found that such prostheses can loosen over time. It is not unusual for the bony structures under the tibial baseplate to respond differently to the loads applied by a patient during walking or other movement. For example, if more of the compact bone had been removed from the medial side of the tibia during resection, the bone under the medial side of the baseplate would be more likely to compress. Over time, the planer resected surface created by the surgeon for the implantation of the prosthesis may deform into a curved surface. Under continued use, the rigid baseplate would tend to rock on the curved surface, ultimately affecting whatever means had been chosen to attach the prosthesis to the tibia. Eventually, the fixation means may fail, in whole or in part, and new surgery may be required.

This problem has been recognized in the past, and some solutions have been proposed which ameliorate the effects described. One solution is to provide separate structures for the medial and lateral condyles. Such a solution is shown, for example, in U.S. Pat. No. 3,774,244 to Walker, or U.S. Pat. No. 4,034,418 to Jackson or U.S. Pat. No. 4,085,466 to Goodfellow. To implant these structures, however, requires that four cooperating structures be implanted, two on the tibia and two on the femur. The possibility of an error in implantation is increased over a unitary construction.

Another partial solution is inherent in U.S. Pat. No. 4,711,639 to Grundei. Grundei proposed a unitary baseplate with two separate articulating surfaces. A small amount of play in the attachment between the articulating surfaces and the baseplate would permit each surface to flex up and down slightly. We find, however, that this solution is inadequate because the tibial prosthesis is only loaded in compression provisioned for separate articulating surfaces, therefore, does not change the action of the baseplate and degradation of the attachment means is still possible.

U.S. Pat. No. 4,883,488 to Bloebaum, et al., reduces the difficulties of implantation by connecting two baseplates together with a slide key. A separate articulating surface is provided for each baseplate.

Another proposed solution is represented by U.S. Pat. No. 4,673,407 to Martin. Martin discloses a prosthesis fixation apparatus comprising a low modulus spring interposed between a cancellous bone screw and a baseplate. This seeks to reduce the affect of rocking on the fixation means, but it does not eliminate or reduce rocking of the baseplate to a significant extent. Bone ingrowth into such a prosthesis would be impeded by the rocking action.

SUMMARY OF OUR INVENTION

We have invented a tibial prosthesis with independent medial and lateral baseplates. The baseplates can be coupled together for simultaneous implantation using an implantation apparatus which we have designed. Both the medial and the lateral baseplates can be reliably positioned on a resected surface of a tibial head. A high-molecular weight polyethylene upper part with articulating surface can then be attached both to the baseplates and to the tibia.

The resulting prosthesis can conform to the stable condition of the tibia without rocking in the baseplates. Bony ingrowth from the tibial head into special surfaces of the baseplates securely attaches the baseplates to the tibial head and the possibility of diminished fixation is reduced.

It is an important object of our invention to overcome the limitations of the prior art by providing a tibial prosthesis which ameliorates the affect of rocking.

It also an object of our invention to provide a prosthesis which can be reliably implanted on a resected tibia.

Another important object of our invention is to provide a tibial prosthesis wherein the component parts cooperate with one another.

It is also an object of our invention to provide a tibial prosthesis wherein the baseplates can accept bony ingrowth.

Another important object of our invention is to provide a tibial prosthesis having independent medial and lateral baseplates connected by a single plasticly deformable articulating surface.

These and other objects and advantages of our invention will be apparent from the following detailed description of our preferred embodiment, together with the accompanying drawings.

BRIEF DESCRIPTION OF THE DRAWINGS

FIG. 9 is a perspective view of an apparatus for implanting the medial and lateral baseplates.

FIG. 10 is a through section of the apparatus of FIG. 9, taken along line 10—10.

FIG. 8 is a perspective view of a guide assembly for use in preparing a resected surface on a tibia.

DETAILED DESCRIPTION OF OUR INVENTION

Figure 1:
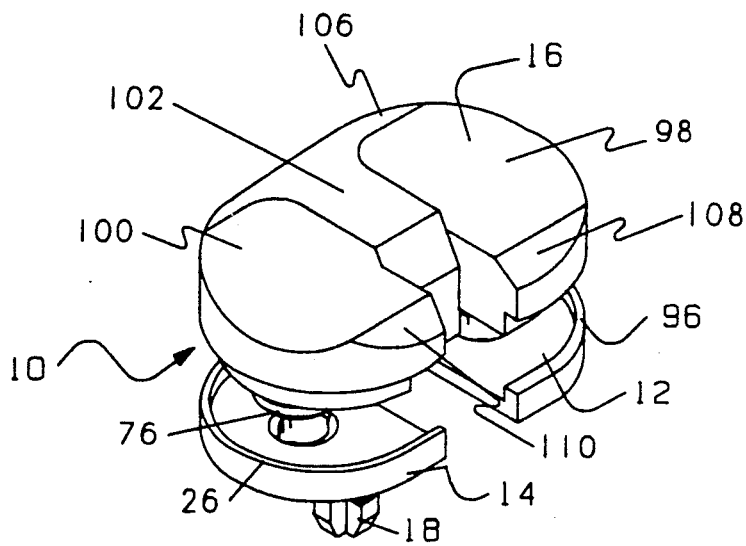
FIG. 1 is a perspective exploded view of a tibial prosthesis according to our invention, showing an upper part with articulating surface and medial and lateral baseplates.

In the accompanying drawings, like numerals are used to designate like parts throughout. In FIG. 1, a tibial prosthesis 10 is shown in exploded perspective view. According to our invention, the tibial prosthesis 10 comprises a medial baseplate 12 and a separate and independent lateral baseplate 14. An upper part with articulating surface 16 connects the two baseplates 12, 14. A cruciate stem 18 attaches the upper part 16 directly to a patient's tibia.

Figure 2:
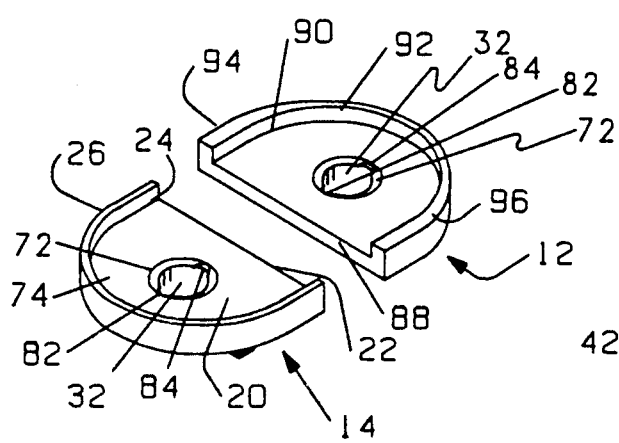
FIG. 2 is a perspective view of the medial and lateral baseplates of FIG. 1.

As shown in FIG. 2, the lateral baseplate 14 comprises an inferior plate 20 with a linear edge 22 adjacent the medial baseplate 12 and an arcuate edge 24 connecting the ends of the interior edge 22. A raised lip 26 is connected to the arcuate edge 24 and stands proud of the inferior plate 20. As shown in the inverted view of FIG. 3, there is a cylinder 28 on a bottom side 30 of the inferior plate 20. The cylinder 28 has a cavity 32 which opens through the inferior plate 20. In our preferred embodiment, this cavity 32 is cylindrical in form. A smaller bore 34 is drilled through bottom 36 of the cylinder 28 to attach the lateral baseplate 14 to the tibia.

A cancellous bone screw (not shown) may be affixed through the bore 34. On areas of the plate which will be adjacent to bone when the prosthesis 10 is implanted porous areas, such as areas 38, 40, 42 and 44, may be provided to accept bony ingrowth. In addition, anti-rotation pins 48, 50 on the bottom side 30 of the inferior plate 20 may also be used to secure the baseplate 14 to a tibia.

In our preferred embodiment of our invention, the cylinder 28 is utilized because, as will be more fully explained below, an appropriate cavity can be relatively easily milled into the tibial head. An alternative configuration is shown in FIG. 4. In the embodiment of FIG. 4, a frustro-conical or truncated cone eminence 52 replaces the cylinder 28. A central bore 54 may still be provided as well additional lateral bores 56, 58. The lateral bores 56, 58 may also be used to assist in the placement of the prosthesis 10, as will be explained below. As in the embodiment of FIG. 3, porous areas 60, 62 are provided to receive bony ingrowth. Stabilizing pins 64, 66, 68, 70 may be provided to further secure the baseplate to the tibial head.

Referring again to FIG. 2 it can be seen that the cavity 32 has a lip 72 adjacent an upper surface 74 of the inferior plate 20. The lip 72 engages circular tabs 76, 78 on the upper part 16. The lip 72 is also used to engage an implantation apparatus 80, shown in FIG. 9. The operation of the implantation apparatus 80 will be more fully explained below. To facilitate the use of the apparatus 80 two opposed slots 82, 84 are milled through the lip 72.

The medial baseplate 12 is substantially the mirror image of the lateral baseplate 14. It has an inferior plate 86 defined by an interior edge 88 adjacent the lateral baseplate 14 and an arcuate edge 90 which connects the ends of the interior edge 88. A lip 92 is attached to the inferior plate 86 along the arcuate edge 90.

In the preferred embodiment of our invention, the arcuate edge 24 of the lateral baseplate 14 and the arcuate edge 90 of the medial baseplate 12 are of identical size and shape, but of opposite hand. This makes it possible to use a single implantation apparatus 80 for either a left or right knee. We considerate it important, however, to provide a more anatomically accurate articulating surface by making the medial portion of the articulating surface somewhat larger than the lateral surface. This is accomplished by widening the wall 92 at its ends 94, 96. The medial baseplate is substantially identical to the lateral baseplate with respect to its lower surface and the cavity, so we will not repeat the description of these parts.

Figure 5:
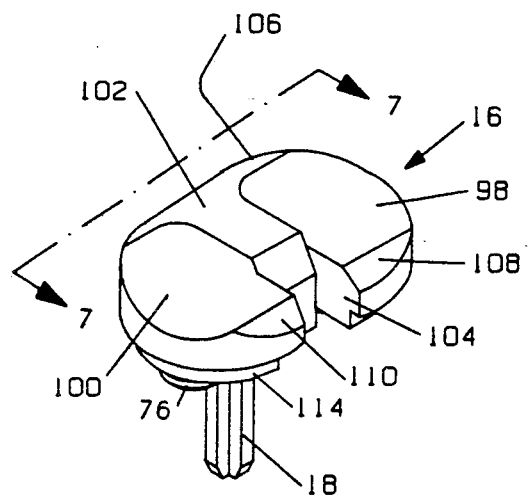
FIG. 5 is a perspective view of the upper part with articulating surface of FIG. 1.
Figure 6:
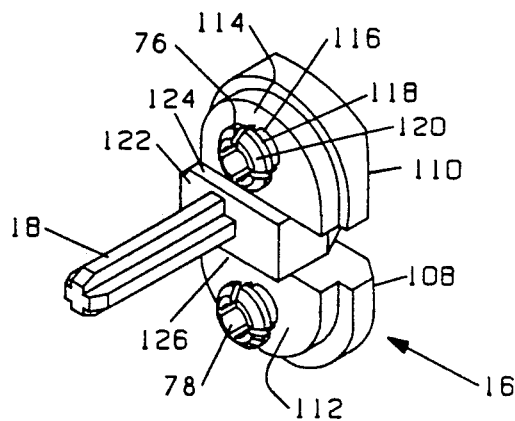
FIG. 6 is an inferior perspective view of the upper part of FIG. 5.
Figure 7:
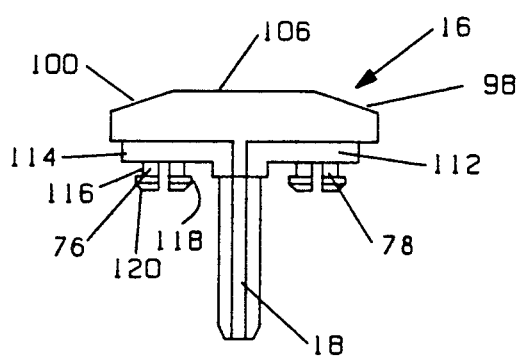
FIG. 7 is a front plan view taken of the direction of line 7—7 of FIG. 5.

The upper part with articulating surface 16 is shown in detail in FIGS. 5-7. A medial articulating surface 98 is separated from a lateral articulating surface 100 by a central prominence 102. Between the two articulating surfaces 98, 100 and posterior to the prominence 102 there is a notch 104 through which ligaments may pass when the prosthesis is implanted in a patient's knee. Anterior from the articulating surfaces 98, 100 there is an elevated ridge 106. A posterior edge of each articulating surface 98, 100 is chamfered 108, 110. As seen in FIGS. 6 and 7, there is a medial baseplate insert 112 and a lateral baseplate 114 configured to mate with the medial baseplate 12 and the lateral baseplate 14 respectively. As mentioned heretofore the tabs 76, 78 are provided to snap into the baseplates 12, 14. In our preferred embodiment, the tabs 76, 78 each comprise four quarter cylinders 116 with a circumferential lip 118 and chamfered lower exterior edge 120. The quarter cylinders 116 are grouped together in sets of four to form a circular configuration which can flex radially inward to engage the lips 72 in the cavities.

Between the medial baseplate insert 112 and the lateral baseplate insert 114 is a ridge 122 having spaced parallel linear edges 124, 126 for engaging the interior edges 88, 22 of the medial baseplate 12 and the lateral baseplate 14 respectively. The cruciate stem 18 extends from the ridge 122 in a direction generally perpendicular to the baseplate inserts.

The tibial baseplates 12, 14 are preferably manufactured from a rigid biocompatible metal, such as titanium. Each is free to settle on its adjacent bone surface and to form a secure and permanent bond with the bone surface. Even if the shape of the bone surface changes after implantation, due to the different character of the bone across the surface, continuing disease, or unequal loading, the baseplates will not transmit rocking forces from one to the other. Consequently, the baseplates will remain securely implanted on the tibia and bone growth into the porous surfaces may be expected to enhance the long-term stability of the prosthesis. The upper part 16, on the other hand, is preferably composed of high molecular weight polyethylene and is, therefore, slightly plastically deformable in addition, the connection between the baseplates and the inserts should be non-rigid. There should be some play between the tabs and the cavities so that there can be some shifting between the baseplates and the inserts both for the long-term configuration of the prosthesis the surrounding bone adjusts to the presence of the prosthesis and over the short-term as the prosthesis is loaded and unloaded by the patient's movement.

In order to permit reliable, accurate installation of the prosthesis 10, we have also invented a method and apparatus for implanting the prosthesis. To implant the prosthesis a surgeon should first prepare the head of the tibia by resecting a planer surface thereon. A surgeon may choose to use a sagittal saw to freely resect the tibia, or may choose to use the guidance of jigs to establish a more accurate surface. These techniques are known to those skilled in the art and will not be further described here. After the flat resected surface has been established on the head of the tibia, the surgeon should place a guide assembly 130 on the surface. See FIG. 8. The guide assembly 130 comprises a handle 132 and an asymmetric template 134. The template 134 has arcuate lateral portion 136 opposite a relatively larger arcuate medial portion 138. The template 134 can be inverted so that it can be used for either the right or left knees. Four drill bores 140 are provided so that the template 134 can be securely located on the resected surface of the tibia. These drill bores, when the bits have been removed, will provide pilot holes for pins such as pins 48 and 50 shown in FIG. 3. With the template 134 in place, a milling bit (not shown) with a stop depth ridge is inserted into each of two holes 142 and 144 on the lateral and medial sides of the template to produce cylindrical bores of a desired depth for receiving the cylinders of the baseplates, such as cylinder 28 shown in FIG. 3. A cruciate broach, not shown, is driven through a cruciate opening 146 in the template to form a cavity in the bone for receiving the stem 18.

The surgeon can then remove the guide assembly 130 from the tibia. The head of the tibia is now prepared to receive a trial prosthesis which is used to ensure that correct sizes have been selected for implantation. The components of the trial prosthesis are substantially identical to the actual prosthesis 10 which has been heretofore described. The dimensions of the trial prosthesis with respect to the pins, cylinders or the cruciate stem, which would generally affix the prosthesis to the tibia, are slightly smaller than the dimensions of the actual prosthesis 10 so that the trial prosthesis may be removed at an appropriate time. The trial prosthesis is implanted in substantially the same manner as the actual prosthesis 10. This process, therefore, will be described hereafter in connection with the actual prosthesis. Once the trial prosthesis has been implanted, the surgeon will ordinarily test the motion of the limb to ensure proper sizing and positioning has been achieved. Then the trial prosthesis would be removed and the actual prosthesis installed.

We will now described the implantation of the prosthesis 10. To implant the prosthesis 10 accurately, we have designed the implantation apparatus 80 shown in FIGS. 9 and 10. This apparatus comprises a symmetrical baseplate 148 which has two parallel edges 150, 152 connected by a semi-circular edges 154, 156. A shaft 158 is attached to the center of the plate 148 and perpendicular to the plane thereof. A handle 160 may be provided for extracting either the trial or actual baseplates as will be explained hereafter. A hammer plate 162 is attached to one end of the shaft 158. Two quick-release latches 164, 166 are provided for engaging the medial baseplate 12 and the tibial baseplate 14. Each of these latches 164, 166 is similar and can best be described with reference to FIG. 10. Each latch comprises a circular chamber 168 containing a central shaft 170 with a T-bar 172 at a distal end thereof. The shaft 170 passes through the plate 148 and can both slide axially and be rotated about its longitudinal axis. A knob 171 is provided at a proximal end of the shaft. Inside the cylinder 168 there is a spring 174 which holds the T-bar in a retracted position against the plate 148. We prefer to provide small stops 176 on the bottom of the plate 148 so that the T-bars 172 can be easily oriented in a desired position by touch.

To place the baseplates on the apparatus 80 the T-bars 172 are oriented so that they will align with the notches 82, 84 in the baseplate. The baseplate is then placed against the plate 148 so that the arcuate edge, for example arcuate edge 24, engages a semi-circular edge, for example edge 156, of the plate. The knob 171 can then be pushed and turned 90° so that the T-bar 172 engages the lip 72 in the baseplate. The spring 174 then holds the baseplate against the apparatus 80. With both baseplates attached to the apparatus 80, they can be simultaneously and accurately positioned on the resected surface of the tibia.

Figure 3:
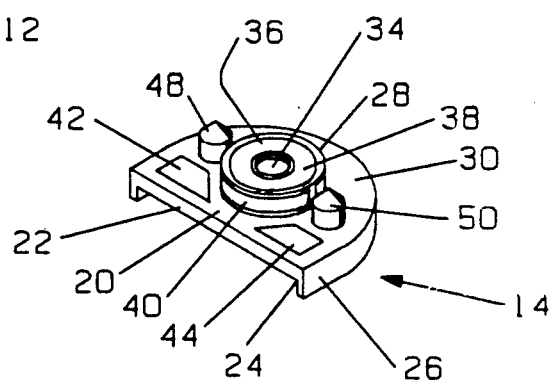
FIG. 3 is an inverted perspective view of the lateral baseplate of FIG. 2.
Figure 4:
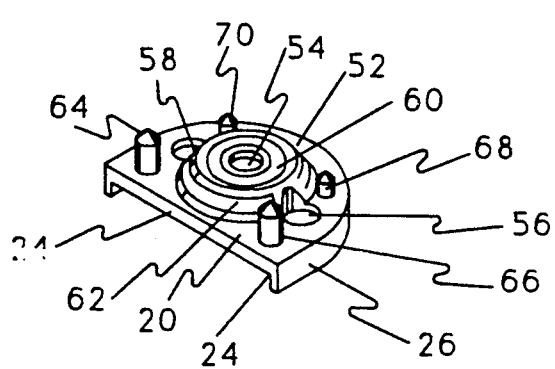
FIG. 4 is an inverted perspective view of an alternative embodiment of a baseplate.

Using our preferred configuration shown in FIG. 3, the pins 48 and 50 could be aligned with the pilot holes made through the bores 140 of the guide 130. The surgeon can then hammer the prosthesis into place by pounding on the hammer plate 162. The trial prosthesis can be extracted by pulling on the handle 160. If necessary, the actual prosthesis 10 can also be extracted in a similar fashion. Once the actual baseplates 12, 14 are implanted, a press fit will hold the baseplates in place. Additional fixation means may also be employed as, for example, bone cement, or a cancellous bone screw through the bore 34 of the embodiment of FIG. 3 or through the bores 54, 56 and 58 of the embodiment of FIG. 4. Once the baseplates are in position, the articulating surface insert 16 can be pressed into position by driving the cruciate stem 18 into the cavity prepared for it and by snapping the tabs 76, 78 into their respective cavities in the medial and lateral baseplates.

Our invention may be embodied in other specific forms without departing from the spirit or essential characteristics thereof. The present embodiment is therefore considered in all respects to be illustrative and not restrictive, the scope of our invention being indicated by the appended claims rather than by the foregoing description and all changes which come within the meaning and range of the equivalency of the claims are therefore intended to be embraced therein.

We claim as our invention:

1. A tibial prosthesis comprising
   a separate medial baseplate adapted to be affixed to a medial surface at a head of a patient's tibia, said medial baseplate having a bottom side and a top side;
   means on said bottom side of said medial baseplate for independently securing said baseplate to said tibia;
   a separate lateral baseplate adapted to be affixed to a lateral surface at the head of the tibia, said lateral baseplate having a bottom side and a top side;
   means on said bottom side of said lateral baseplate for independently securing said baseplate to said tibia; and
   an upper part having medial and lateral articulating surfaces and connected to both the medial baseplate and the lateral baseplate, respectively, at the top sides thereof.

2. The tibial prosthesis according to claim 1 wherein the upper part is plastically deformable.

3. The tibial prosthesis according to claim 2 wherein the upper part further comprises means for attaching the upper part to the head of the tibia.

4. The tibial prosthesis according to claim 3 wherein the attaching means comprise a cruciate stem.

5. The tibial prosthesis according to claim 1 wherein each of the baseplates further comprises means for releasibly attaching the respective baseplate to means for securing the baseplates in fixed relationship to each other during implantation.

6. The tibial prosthesis according to claim 1 wherein each baseplate further comprises means for forming an interference connection with the head of the tibia.

7. The tibial prosthesis according to claim 6 wherein the connection forming means comprise a cylinder.

8. The tibial prosthesis according to claim 6 wherein the connection forming means comprises a truncated cone.

9. The tibial prosthesis according to claim 1 further comprising connecting means for making a non-rigid connection between the upper part and at least one of the baseplates.

10. The tibial prosthesis according to claim 9 wherein the upper part is plastically deformable.

11. The tibial prosthesis according to claim 10 wherein the upper part further comprises means for attaching the upper part to the head of the tibia.

12. The tibial prosthesis according to claim 11 wherein the attaching means comprise a cruciate stem.

13. The tibial prosthesis according to claim 9 wherein each of the baseplates further comprises means for releasibly attaching the respective baseplate to means for securing the baseplates in fixed relationship to each other during implantation.

14. The tibial prosthesis according to claim 13 wherein each baseplate further comprises means for forming an interference connection with the head of the tibia.

15. The tibial prosthesis according to claim 14 wherein the connection forming means comprise a cylinder.

16. The tibial prosthesis according to claim 14 wherein the connection forming means comprise a truncated cone.

17. The tibial prosthesis according to claim 9 wherein each baseplate further comprises means for forming an interference connection with the head of the tibia.

18. The tibial prosthesis according to claim 17 wherein the connection forming means comprise a cylinder.

19. The tibial prosthesis according to claim 18 wherein the connection forming means comprise a truncated cone.

20. The tibial prosthesis according to claim 9 wherein the connecting means comprises first connecting means for making a non-rigid connection between the upper part and the medial baseplate and second connecting means for making a non-rigid connection between the upper part and the lateral baseplate.

21. The tibial prosthesis according to claim 20 wherein the upper part is plastically deformable.

22. The tibial prosthesis according to claim 21 wherein the upper part further comprises means for attaching the upper part to the head of the tibia.

23. The tibial prosthesis according to claim 22 wherein the attaching means comprise a cruciate stem.

24. The tibial prosthesis according to claim 20 wherein each of the baseplates further comprises means for releasibly attaching the respective baseplate to means for securing the baseplates in fixed relationship to each other during implantation.

25. The tibial prosthesis according to claim 24 wherein each baseplate further comprises means for forming an interference connection with the head of the tibia.

26. The tibial prosthesis according to claim 25 wherein the connection forming means comprise a cylinder.

27. The tibial prosthesis according to claim 25 wherein the connection forming means comprise a truncated cone.

28. The tibial prosthesis according to claim 20 wherein each baseplate further comprises means for forming an interference connection with the head of the tibia.

29. The tibial prosthesis according to claim 28 wherein the connection forming means comprise a cylinder.

30. The tibial prosthesis according to claim 29 wherein the connection forming means comprise a truncated cone.

31. The tibial prosthesis according to claim 20 wherein the first and second connecting means each comprise a male snap connector on the upper part and a female connector on the medial and lateral baseplates respectively.

32. The tibial prosthesis according to claim 31 wherein the upper part is plastically deformable.

33. The tibial prosthesis according to claim 32 wherein the upper part further comprises means for attaching the upper part to the head of the tibia.

34. The tibial prosthesis according to claim 33 wherein the attaching means comprise a cruciate stem.

35. The tibial prosthesis according to claim 31 wherein each of the baseplates further comprises means for releasibly attaching the respective baseplate to means for securing the baseplates in fixed relationship to each other during implantation.

36. The tibial prosthesis according to claim 35 wherein each baseplate further comprises means for forming an interference connection with the head of the tibia.

37. The tibial prosthesis according to claim 36 wherein the connection forming means comprise a cylinder.

38. The tibial prosthesis according to claim 36 wherein the connection forming means comprise a truncated cone.

39. The tibial prosthesis according to claim 31 wherein each baseplate further comprises means for forming an interference connection with the head of the tibia.

40. The tibial prosthesis according to claim 39 wherein the connection forming means comprise a cylinder.

41. The tibial presthesis according to claim 39 wherein the connection forming means comprise a truncated cone.

42. A method for implanting a prosthetic tibia comprising the steps of:
   resecting a generally flat surface at a head of a tibia;
   preparing the surface to receive the tibial implant;
   attaching a medial baseplate and a lateral baseplate to an apparatus adapted to hold the separate medial baseplate and the separate lateral baseplate in fixed relationship to each other;
   securing the medial baseplate and the lateral baseplate to the resected surface;
   removing the apparatus from the baseplates; and
   attaching an upper part having medial and lateral articulating surfaces to both the medial baseplate and the lateral baseplate, respectively.

43. The method according to claim 42 wherein the step of attaching the upper part further comprises affixing the upper part to the tibia.

44. The method according to claim 43 wherein the step of affixing the upper part to the tibia comprises driving a cruciate stem into the tibia.

45. The method according to claim 42 wherein the preparing step further comprises
   placing a template on the resected surface;
   milling cavities into the tibia, said cavities being adapted to receive means on the baseplates for affixing the respective baseplates to the tibia; and
   removing the template.

46. The method according to claim 45 wherein the step of securing the medial and lateral baseplates comprises pressing the affixing means into a cavity and forming an interference fit between the tibia and the affixing means.

47. The method according to claim 46 wherein the preparing step further comprises
   attaching a medial trial baseplate and a lateral trial baseplate to the holding apparatus;
   securing the medial trial baseplate and the lateral trial baseplate to the resected surface;
   removing the apparatus from the trial baseplates;
   attaching a trial upper part having an articulating surface to both the medial trial baseplate and the lateral trial baseplate to form a trial tibial prosthesis;
   testing for proper articulation in the patient's knee; and removing the trial prosthesis.

48. The method according to claim 47 wherein the step of attaching the upper part further comprises affixing the upper part to the tibia.

49. The method according to claim 48 wherein the step of affixing the upper part to the tibia comprises driving a cruciate stem into the tibia.

* * * * *